United States Patent
Neijzen et al.

(10) Patent No.: US 9,557,287 B2
(45) Date of Patent: Jan. 31, 2017

(54) CARTRIDGE FOR PROCESSING A FLUID

(71) Applicant: KONINKLIJKE PHILIPS N.V., Eindhoven (NL)

(72) Inventors: Jacobus Hermanus Maria Neijzen, Heeze (NL); Toon Hendrik Evers, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 109 days.

(21) Appl. No.: 14/373,230

(22) PCT Filed: Jan. 18, 2013

(86) PCT No.: PCT/IB2013/050491
§ 371 (c)(1),
(2) Date: Jul. 18, 2014

(87) PCT Pub. No.: WO2013/111042
PCT Pub. Date: Aug. 1, 2013

(65) Prior Publication Data
US 2015/0014185 A1 Jan. 15, 2015

Related U.S. Application Data

(60) Provisional application No. 61/589,917, filed on Jan. 24, 2012.

(51) Int. Cl.
*G01N 27/40* (2006.01)
*B01L 3/00* (2006.01)
*G01N 33/49* (2006.01)

(52) U.S. Cl.
CPC ......... *G01N 27/40* (2013.01); *B01L 3/502715* (2013.01); *G01N 33/49* (2013.01);
(Continued)

(58) Field of Classification Search
CPC ............... B01L 2300/0681; B01L 2300/0867; B01L 2300/0887; B01L 2300/0654; B01L 2300/0816; B01L 2300/0825; B01L 2300/087; B01L 2300/0636; B01L 2300/0809; B01L 2300/0864; B01L 2300/1805; B01L 2300/048; B01L 2300/0645; B01L 2300/0829; B01L 2300/0932; B01L 2300/0851; B01L 2300/123; B01L 2300/1822; B01L 2300/1827; B01L 2300/1861; B01L 2200/027; B01L 2200/10; B01L 2200/04; B01L 2200/0605; B01L 2200/0647; B01L 2200/0684; B01L 2200/0689; B01L 2200/141; B01L 2200/147; B01L 2200/148; B01L 2400/0406; B01L 2400/0487; B01L 2400/0683; B01L 2400/0688; B01L 2400/0409; B01L 2400/043; B01L 2400/0481; B01L 2400/049; B01L 2400/0677; B01L 2400/084; B01L 3/5023; B01L 3/5025; B01L 3/502738; B01L 3/021; B01L 3/0262; B01L 3/502; B01L 3/5021; B01L 3/502723; B01L 3/502746; B01L 3/5029; B01L 3/505; B01L 3/527; B01L 7/5255; B01L 9/527; G01N 33/491; G01N 33/54366; G01N 33/5438; G01N 1/28; G01N 1/34; G01N 1/38; G01N 2021/0321; G01N 2021/0325; G01N 2021/0346; G01N 2021/0357; G01N 2021/0378; G01N 2035/00158; G01N 2035/0097; G01N 21/0303; G01N 21/552; G01N 21/76; G01N 21/7703; G01N 2333/4737; G01N 2333/71; G01N 2333/9129; G01N 2458/30; G01N 27/30; G01N 27/3271; G01N 27/3272; G01N 27/745; G01N 33/5302; G01N 33/5304; G01N 33/54326; G01N 33/54386; G01N 33/558; G01N 33/56966; G01N 35/028; B01J 19/0046; B01J 2219/00283; B01J 2219/00292; B01J 2219/00371; B01J 2219/00385; B01J 2219/00466; B01J 2219/00495; B01J 2219/005; B01J 2219/00653; B01J 2219/00693; B01J 2219/00702; B01J 2219/00725; B01J 2219/0074
See application file for complete search history.

(56) References Cited

U.S. PATENT DOCUMENTS

| | | |
|---|---|---|
| 6,106,732 A | 8/2000 | Johnston et al. |
| 2007/0134810 A1 | 6/2007 | Yang et al. |

(Continued)

FOREIGN PATENT DOCUMENTS

| | | |
|---|---|---|
| WO | WO2008072156 | 6/2008 |
| WO | 2010133997 A1 | 11/2010 |
| WO | WO2010133997 | 11/2010 |

*Primary Examiner* — J. Christopher Ball

(57) ABSTRACT

The invention relates to a cartridge (790) for processing a fluid comprising (i)a pre-treatment fluidic system with an inlet (710) via which the fluid can be supplied and at least
(Continued)

one primary processing chamber (712) in which said fluid can be processed; (ii) a post-treatment fluidic system with at least one secondary processing chamber (755) in which fluid can be processed; (iii) a fluid-treatment element (701) that is permeable to at least a part oft he fluid and that couples the post-treatment fluidic system to the pre-treatment fluidic system. The fluid-treatment element may particularly be a filter material (701) integrated into at least one foil (702, 703, 704).

18 Claims, 8 Drawing Sheets

(52) U.S. Cl.
CPC . *B01L 2200/027* (2013.01); *B01L 2200/0631* (2013.01); *B01L 2200/10* (2013.01); *B01L 2300/0645* (2013.01); *B01L 2300/0681* (2013.01); *B01L 2300/0816* (2013.01); *B01L 2300/0864* (2013.01); *B01L 2300/0887* (2013.01); *B01L 2400/0406* (2013.01); *Y10T 137/0318* (2015.04); *Y10T 137/8158* (2015.04)

(56) References Cited

U.S. PATENT DOCUMENTS

| | | |
|---|---|---|
| 2007/0184547 A1 | 8/2007 | Handique et al. |
| 2007/0292858 A1 | 12/2007 | Chen et al. |
| 2009/0065357 A1 | 3/2009 | Glezer et al. |
| 2009/0087859 A1 | 4/2009 | Johnson |
| 2009/0088336 A1 | 4/2009 | Burd et al. |
| 2010/0310423 A1 | 12/2010 | Nieuwenhuis |
| 2011/0005341 A1 | 1/2011 | Neijzen et al. |
| 2013/0112612 A1 | 5/2013 | Blankenstein et al. |

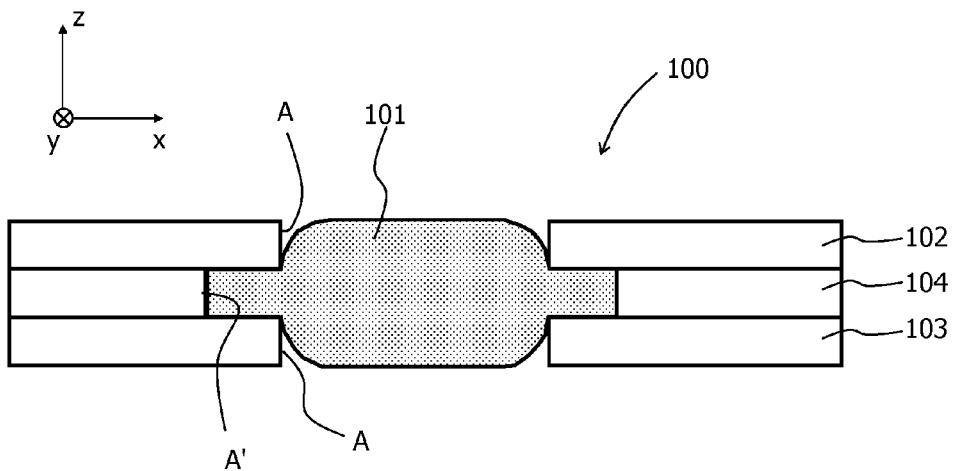
Fig. 1
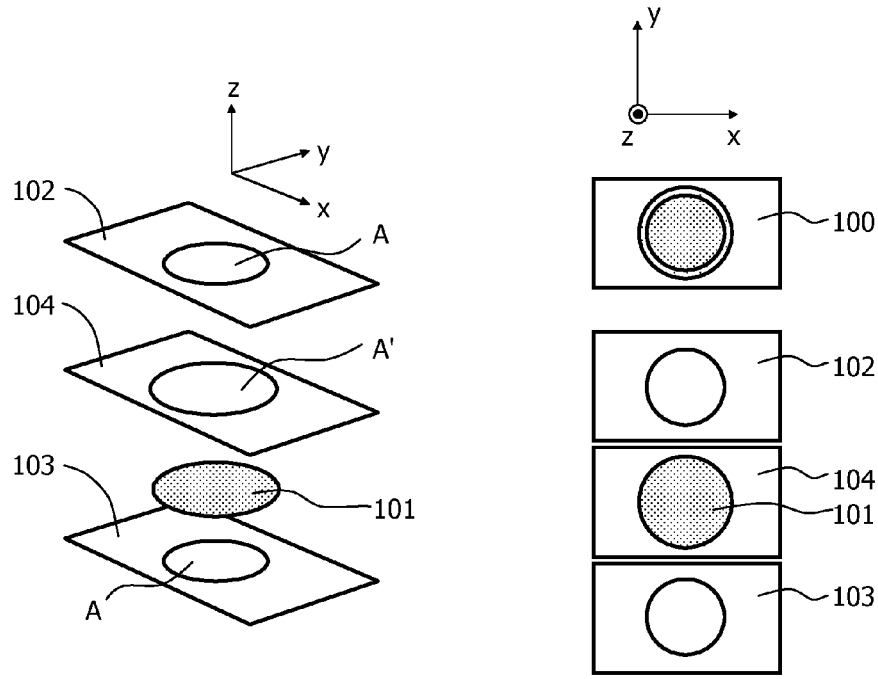
Fig. 2
Fig. 3

CARTRIDGE FOR PROCESSING A FLUID

This application is the U.S. National Phase application under 35U.S.C. §371of International Application Ser. No. PCT/IB2012/050491, filed on Jan. 18, 2013, which claims the benefit of U.S. application Ser. No. 61/589,917,filed on Jan. 24, 2012. These application are hereby incorporated by reference herein.

FIELD OF THE INVENTION

The invention relates to a cartridge and a method for processing a fluid, particularly for filtering a biological sample like blood.

BACKGROUND OF THE INVENTION

The US 2011/0005341 A1 discloses a filtering apparatus comprising a filter material that is attached to an adhesive capillary structure made of a double-sided tape. A sample deposited on the filter material passes said material and enters the capillary structure for further investigation.

SUMMARY OF THE INVENTION

It is an object of the invention to provide means that allow for a more efficient processing of small volumes of a fluid, for example of blood samples.

This object is achieved by a cartridge according to claim 1 and a method according to claim 2. Preferred embodiments are disclosed in the dependent claims.

A cartridge according to a first aspect of the invention serves for the processing of a fluid, for example for the examination of a biological fluid like blood, saliva, or urine. The cartridge comprises the following components:

a) A first fluidic system having an inlet at which the fluid to be processed can be supplied and at least one "primary" processing chamber for the processing of said supplied fluid. For the purpose of reference, this first fluidic system will in the following be called "pre-treatment fluidic system".

b) A second fluidic system, called "post-treatment fluidic system" in the following, comprising at least one "secondary" processing chamber for the processing of fluid.

c) A fluid-treatment element that is permeable to at least a part of the fluid to be processed and that connects the aforementioned pre-treatment fluidic system to the post-treatment fluidic system. This means that fluid which has been supplied to the pre-treatment fluidic system can enter the post-treatment fluidic system via the fluid-treatment element. As its name indicates, an interaction shall take place between this fluid-treatment element and the fluid when the latter passes through the element, resulting in a certain "treatment" of the fluid. Accordingly, fluid entering the fluid-treatment element will in the following also be called "raw fluid", while fluid leaving it is called "treated fluid".

According a second aspect, the invention relates to a method for the processing of a fluid in a cartridge of the kind described above, wherein said method comprises the following steps:

a) Introducing into the inlet of the cartridge a quantity of the fluid to be processed that fills both the pre-treatment fluidic system and the post-treatment fluidic system. As a result, the pre-treatment fluidic system will hence be filled with raw fluid and the post-treatment fluidic system with treated fluid.

b) Processing the (raw) fluid in the primary processing chamber of the cartridge.

c) Processing the (treated) fluid in the secondary processing chamber of the cartridge.

It should be noted that different fractions of the introduced fluid will usually be processed in the primary and the secondary processing chamber, respectively. This means that a given part (e.g. a molecule) of the fluid is processed in either the primary processing chamber or in the secondary processing chamber, but not (sequentially) in both chambers. Moreover, the processing in the primary and the secondary processing chambers will typically take place simultaneously (at least for a part of their duration) and comprise different procedures.

The cartridge and the method have the advantage that they allow for the parallel processing of a given quantity of fluid in a raw stage and a treated stage. This is achieved by the provision of primary and secondary processing chambers that are separated by the fluid-treatment element. Hence the fluid that has been introduced into the inlet is split into a raw fraction and a treated fraction which can then be processed accordingly.

The cartridge and the method are different realizations of the same inventive concept, i.e. the provision of primary and secondary processing chambers that are separated by the fluid-treatment element. Explanations and definitions provided for one of these realizations are therefore valid for the other realization, too. In the following, various preferred embodiments of the invention will be described that apply to both the cartridge and the method described above.

The cartridge and the method are preferably applied for the processing of small quantities of fluid, for example of biological samples that are only available in limited amounts. Accordingly, the total volume of the pre-treatment fluidic system and the post-treatment fluidic system together (and the quantity of fluid introduced in step a) of the method) is preferably smaller than about 500 µl, most preferably smaller than about 50 µl. Such a small total volume can completely be filled for instance by a droplet of blood taken from a fingerprick.

The processing of the raw fluid in the primary processing chamber may for example comprise electrochemical measurements, electrical impedance or heat conduction measurements and/or optical or spectroscopic measurements (e.g. diffuse reflectance, extinction).

The secondary processing chamber may optionally comprise a transparent side face that allows for the optical examination of the treated fluid in said processing chamber. This optical examination hence constitutes an example of the processing step c) of the method. It may particularly be limited to a thin fluid layer directly adjacent to the transparent side face. This is for example realized by creating an evanescent optical field in the fluid and by observation of for example scattered light, fluorescence light, or frustrated total internal reflection (FTIR). Accordingly, the transparent side face is for example designed such that it allows for an irradiation with an external light beam and preferably also for the observation of scattered and/or totally internally reflected light resulting therefrom. More details about FTIR measurements may be found in the WO 2008/072156 A2, which is incorporated into the present text by reference.

The fluid-treatment element may in general be any device that manipulates, processes or treats the fluid at hand when this passes through the element. In a typical example, the fluid-treatment element may be or comprise a filter element that is designed to retain target components of the fluid.

The fluid to be processed may preferably be blood. In medical procedures, the required quantity of blood samples should be as small as possible in order to minimize inconvenience caused to a patient. At the same time, a large number of different detection procedures shall usually be executed with such a sample, wherein some of these procedures require a treatment (like filtering of cells to separate plasma from whole blood) while others do not. Both requirements can optimally be met by the cartridge and the method of the present invention.

In the following, preferred embodiments of the invention will be described that are based on a cost-effective manufacturing approach for the fluid-treatment element when the latter is designed as a filter.

Accordingly, the invention comprises a filter unit for filtering a fluid, for example a liquid of biological origin like blood, saliva, or urine. As usual, the process of "filtering" shall comprise that certain target components of the fluid are retained by the filter unit due to their specific physical and/or chemical properties (e.g. their size). The filter unit comprises the following components:

a) At least one foil that is impermeable to the fluid to be filtered and that comprises at least one aperture or opening.

In this context, the term "foil" shall denote as usual a sheet or layer of some (solid) material, wherein said material is preferably distributed homogeneously in said layer. Moreover, the layer will typically have a uniform thickness and will be flat in the sense that its thickness is much smaller than its dimensions in the directions orthogonal to the thickness (i.e. width and length). Typically, the thickness will be in the range of 10 μm to 1000 μm, while length and width of the foil are in the range of several millimeters up to several centimeters. Furthermore, a foil is typically a self-supporting structure and flexible to a certain degree such that it is for example possible to bend it into a desired three-dimensional configuration or to coil it up.

b) A filter material that is permeable to at least a part of the fluid and that is integrated into the aforementioned aperture of the foil.

The integration of the filter material into the aperture of a foil means that filter material is (at least partially) located in the same layer as the foil, replacing foil material that has been removed to provide the aperture. Attachment of the filter material to the foil can be achieved in different ways, for example by gluing it to the borders of the aperture. Typically the aperture is completely filled by the filter material, implying that any fluid which passes through the aperture has to flow through the filter material. When the fluid permeates the filter material, an intimate interaction between filter material and fluid can take place by which the intended retention of target components from the fluid can be achieved. Target components like biological cells can for example be retrained by a porous filter material having a pore size smaller than the cell diameter.

By the integration of a filter material into the aperture of a foil, a filter unit is achieved that can substantially be processed in the same way as a foil. Such a filter unit can for example be produced and/or attached to other components by cost-effective manufacturing procedures like roll-to-roll techniques.

The invention further comprises a cartridge for processing a fluid, said cartridge comprising a substantially rigid carrier and a filter unit of the kind described above, wherein the carrier and the filter unit are attached (bonded) to each other.

The rigid carrier provides mechanical stability to the cartridge. Moreover, it may provide additional functions or components like examination chambers for detection processes.

Moreover, the invention comprises a method for manufacturing a filter unit comprising a filter material, particularly a filter unit of the kind described above. The method comprises the following steps, which can be executed in the listed order, in reverse order, or simultaneously:

Bonding of two foils to each other such that they embed a filter material between them.

Providing at least one aperture in each foil at the position of the filter material.

If the aforementioned step is done first, i.e. before the bonding of the two foils, the apertures are provided at the position where the filter material shall be located during the bonding step.

By embedding a filter material between two foils, a sandwich structure is achieved in which said filter material is firmly integrated while being accessible through the apertures in the foils. Moreover, such a procedure is compatible with effective production processes like roll-to-roll manufacturing techniques.

The filter unit, the cartridge that comprises such a filter unit, and the method are different realizations of the same inventive concept, i.e. the integration of a filter material into at least one foil. Explanations and definitions provided for one of these realizations are therefore valid for the other realization, too. In the following, various preferred embodiments of the invention will be described that relate to this filter unit, cartridge, and method.

The foil or at least one of the foils of the filter unit may preferably comprise materials selected from the group consisting of polyethylene (PE), polymethyl methacrylate (PMMA), cyclopolyolefine (COP, COC), polycarbonate (PC), polypropylene (PP), polyethylene terephthalate (PET), polyethylene naphthalate (PEN), polyvinyl chloride (PVC), polyimides (PI), polystyrene and oriented polystyrene (PS, OPS), polyvinylidene chloride (PVDC), polyamides, nylon (e.g. cast, oriented or coex, PA, 6, 11, 12, amorphous, polyarylamide MXD6), polyvinyl butyral (PVB), liquid crystal polymers (LCP), and fluoropolymers (particularly PCTFE).

The kind of the filter material will be chosen in view of the application at hand, i.e. with respect to the fluid to be processed and the target components to be retained. Typically, the filter material will be porous with an average pore size ranging between about 0.1 μm and about 1000 μm. Appropriate filter materials comprise for example asymmetric polysulphone membranes (e.g. Vivid™ Plasma Separation Membrane of Pall Corporation, Port Washington, N.Y., USA; VF blood separation filters of Whatman plc, Maidstone, UK).

As explained in connection with the manufacturing method, a preferred way to integrate filter material into an aperture of a foil is to arrange said filter material between two foils, which will in the following be called "top foil" and "bottom foil" for purposes of reference. The size (area) of the filter material is in this case preferably chosen larger than that of one aperture in one foil, preferably larger than that of both apertures in both foils. The border of the filter material will then be firmly held (sandwiched) between the top and bottom foil.

In a further development of the aforementioned embodiment, the filter material is arranged in the aperture of a third foil, called "intermediate foil" in the following, wherein said intermediate foil is enclosed between the top foil and the bottom foil. The thickness of the intermediate foil is preferably the same as or less than the thickness of the filter material. Moreover, the aperture in the intermediate foil is preferably large enough to completely accommodate the filter material without overlap. As already mentioned, the apertures in the top and bottom foil, on the contrary, are preferably smaller than the area of the filter material. The provision of the intermediate foil has the advantage that the filter material can better be integrated into the stack of foils, particularly without the generation of undesirable dead volumes.

If the filter unit comprises a stack of two or more foils, all these foils may be identical in geometry and material. In an alternative embodiment, there are at least two foils of the stack that have different geometry and/or that consist of different materials. For example, the thickness, the total area, or the aperture size or shape of two foils may be different.

The one or more foils that are comprised by the filter unit may geometrically be layers of uniform thickness. In a preferred embodiment, at least one foil of the filter unit may however comprise one or more cavities, i.e. spaces where foil material is missing in comparison to the geometry of a uniform layer. Cavities in a foil may readily be produced for example by hot embossing. A cavity may for example be generated around the border of an aperture of a foil to create a space in which filter material can be accommodated. Moreover, cavities in a foil may constitute channels, chambers or the like through which fluid can flow for processing purposes.

In a related embodiment, a foil of the filter unit may optionally comprise protrusions that define regions of material additional to the geometry of a uniform layer. This embodiment is largely equivalent to the aforementioned one as a foil with a three-dimensional structure that deviates from a simple uniform layer geometry can be regarded as a foil with cavities (in a thick layer) or a foil with protrusions (from a thin layer). Generally, a structured foil may comprise both cavities and protrusions.

The filter material of the filter unit may preferably have on at least one side a dome shape, i.e. it bulges into one direction out of the plane of the filter unit or its foils, respectively. Such a dome shape is often advantageous during the processing of a fluid. For example, a droplet of a sample deposited onto the filter may more readily be absorbed if the filter material bulges towards the drop. Similarly, a dome shape of the filter material may be used to guarantee contact of the filter material to subsequent components of the filter unit or the cartridge. This minimizes dead volume and ensures that fluid which has passed the filter material is forwarded by capillary forces. It should be noted that the filter material may have a dome shape in one direction only or in two (opposite) directions. In the latter case, the cross section of the filter material within the foil aperture will typically be convex.

In a further embodiment, a holding element may be provided for pressing or biasing the filter material in one given direction. As a consequence of this pressing, the aforementioned dome shape (in one direction) may result. In general, the pressing by the holding element can be used to guarantee a certain geometry of the filter material and/or to guarantee contact between the filter material and subsequent components of the filter unit or the cartridge.

The aforementioned holding element may for example be realized by an additional layer, particularly an additional foil, of the filter unit that presses the filter material in one direction. This realization of the holding element may readily be produced, for instance by the same roll-to-roll processes by which the filter unit itself is manufactured.

In many applications, one side of the filter material will remain accessible during the intended use of the filter unit. Access may for example be necessary to deposit sample fluid onto the filter material. In a preferred embodiment, a side of the filter material that is accessible during use is designed to hold a quantity of a given fluid that ranges between a given minimum and a given maximum quantity, provided that the fluid completely covers the filter material and that it is held by (molecular) adhesion forces only. A design parameter that is relevant for this aim is the size and shape of the aperture in the outer foil which determines the area of the filter material that is directly accessible. Another important design parameter is the surface chemistry at the respective filter side, particularly the chemistry of the associated foil and/or the filter material. The surface of the foil may for example be hydrophobic in order to repel an aqueous fluid like blood. With the described design it can be guaranteed that a desired quantity of blood is taken up by the filter material after the application of an undefined amount of blood to the accessible filter side. If less than the minimum amount of fluid is applied, at least a part of the filter material will not be covered by the fluid, which can readily be detected by visual inspection.

The one or more foils of the filter unit may have just a single aperture at which the filter material is located. In a more elaborate design, the filter material of the filter unit may be covered by a foil with at least two apertures providing access to the same element of filter material. This foil with the several apertures may particularly be arranged on the side of the filter material that remains accessible during use. Using a plurality of small apertures instead of a single large aperture above the filter material helps to prevent an undesired contact between the filter material and large objects, for example instruments or the finger of a user (e.g. during direct uptake of fingerprick blood). Direct touching can be prevented if the apertures are sufficiently small, for example having a diameter of less than about 5 mm.

The filter unit may optionally comprise electrical components, particularly electrical leads, electrodes, and/or an RF ID tag. These components are preferably generated in the same manufacturing procedure as the foil, using for example roll-to-roll techniques. Electrically conductive structures may for example be printed onto a foil comprised by the filter unit.

The carrier of the cartridge may optionally comprise some structure for supporting the filter material of the filter unit. This support may provide mechanical stability to the filter material and contact between the carrier and the filter material.

In general, the carrier may comprise any material or structure that is suited for the intended purpose. In a particular embodiment, the carrier may at least locally be transparent to allow for the optical examination or processing of the applied fluid.

The carrier of the cartridge may optionally comprise at least one cavity for the accommodation of a fluid, wherein said cavity is preferably connected to the filter material. In the latter case, fluid can be transported through the cavity towards the filter material, or fluid that has passed the filter material can be taken up by the cavity for further processing steps. The cavity in the carrier may for instance comprise one or more (elongated) channels for transporting fluid or one or more chambers for accommodating fluid during processing steps.

In a further development of the aforementioned embodiment, at least one cavity of the carrier is covered by a foil of the filter unit that is attached to the carrier. An elaborate structure of cavities (e.g. channels and/or chambers) in the carrier can thus readily be produced, for example by injection molding, as the cavities may initially be open at the side which is later covered by the foil of the filter unit.

According to another preferred embodiment of the invention, a first (micro-) fluidic system is located on a first side of the filter material, and a second (micro-) fluidic system is located on the opposite side of the filter material. For purposes of reference, the first fluidic system will in the following be called "pre-treatment fluidic system", and the second one "post-treatment fluidic system". The names indicate that the pre-treatment fluidic system typically transports raw (untreated) fluid, while the post-treatment fluidic system is only reached by filtered (treated) fluid. The provision of a pre-treatment and a post-treatment fluidic system on opposite sides of the filter material has the advantage that one and the same sample of a fluid can be processed in parallel with and without a filtering step, respectively. Thus it is for example possible to examine whole blood (in the pre-treatment fluidic system) as well as blood plasma (in the post-treatment fluidic system) from a single blood sample.

Depending on the intended application and processing, the aforementioned fluidic systems may individually be designed. In a preferred embodiment, the pre-treatment fluidic system may for example comprise an inlet for fluid, e.g. for a drop of blood. This fluid will then spread in the pre-treatment fluidic system, where certain investigations or processing steps can be done, and also pass through the filter material to the post-treatment fluidic system for the execution of other processing steps.

The pre-treatment fluidic system may for example comprise a processing chamber for the processing of a fluid that has NOT passed the filter material.

Similarly, the post-treatment fluidic system may comprise a processing chamber for the processing of a fluid that has passed the filter material.

According to another embodiment of the invention, the filter unit and/or the carrier comprises a processing chamber that is located adjacent to the filter material and in which fluid can be processed, for example be investigated with respect to the presence of certain target substances. Most preferably, said processed fluid is a fluid which has passed the filter material. Arrangement of a processing chamber directly adjacent to the filter material helps to minimize the required amount of fluid and the time for processing it because losses of material and time during a transport of the fluid (from the filter material to the processing chamber) are avoided.

BRIEF DESCRIPTION OF THE DRAWINGS

These and other aspects of the invention will be apparent from and elucidated with reference to the embodiments described hereinafter.

In the drawings:

FIG. 1 shows a schematic cross section through a first filter unit according to the invention;

FIG. 2 shows an exploded perspective view of the filter unit of FIG. 1;

FIG. 3 shows a top view onto the filter unit of FIG. 1 (top drawing) and top views onto the foils constituting said filter unit (bottom three drawings);

Like reference numbers or numbers differing by integer multiples of 100 refer in the Figures to identical or similar components.

DETAILED DESCRIPTION OF EMBODIMENTS

Figure 4:
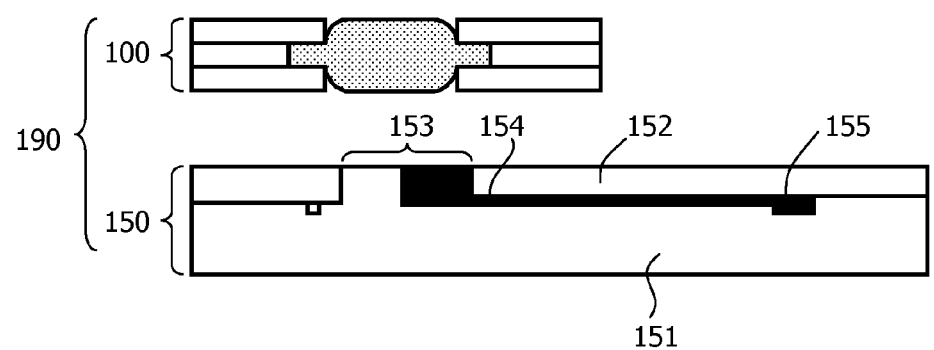
FIG. 4 shows a cross section through a cartridge comprising the filter unit of FIG. 1 before the attachment of the filter unit to the carrier.

Biosensors are known for the detection of specific target molecules in body fluids like saliva, urine, and especially blood. A biosensor platform as it is for example known from the US 2010/0310423 A1 (also called Philips "Magnotech" platform) uses multi-chamber disposable cartridges. Separate detection chambers are used for the selective detection of different target proteins using immunoassays based on magnetic particles and optical detection methods (e.g. frustrated total internal reflection (FTIR), or single bead detection).

In order to reduce costs of the aforementioned biosensors, a more cost effective design of the disposable cartridge is desirable. Preferably the new design should allow for a production based on roll-to-roll manufacturing techniques (e.g. hot embossed foils, lamination, etc.). Thus the easy combination of a number of functions (capillary fluid transport, RF-ID, filter mounting, electrochemistry etc.) in simple subunits can be achieved that can still be combined with injection molded cartridge parts (if necessary, e.g. for sensitive optical detection and/or evanescent field excitation). Another objective is to allow the detection of target molecules in both blood and plasma starting from a limited volume blood sample (fingerprick). Moreover, optimal exploitation of small sample volumes is desirable. According to one aspect, the proposed approach suggests a switch to roll-to-roll processing wherever possible. An advantage of this approach is that some functionalities are already made in roll-to-roll processes (e.g. RF tags), which enables a smooth integration.

An important aspect of the invention is hence a filter mounted in a foil, enabling the use of low-cost roll-to-roll (R2R) production technology. This subunit can be supplemented with other foil based functionalities (e.g. screen printed electrodes, RF-ID tag, capillary channels, hot-embossed structures). The foil based subunit may be combined with an injection molded part (if needed) to form a disposable cartridge. The injection molded part contains the critical functionalities that cannot be realized in R2R technology.

In the following, a number of examples of the combination of a roll-to-roll subunit ("filter unit") and an injection molded part ("carrier") that together form a cartridge for e.g. the Magnotech platform will be described. All examples include a blood separation filter that is mounted using lamination techniques. For some applications the injection molded part can be replaced by a foil based part as well, leading to a fully foil based cartridge.

FIG. 1 shows a filter unit 100 (not to scale) according to a first embodiment of the invention. The coordinate device shown in this Figure applies similarly to FIGS. 4, 5, 8, 9, 10, 12, 14, 17 and 18 (i.e. to all Figures where no other coordinate device is shown). FIGS. 2 and 3 show an exploded view and a top view of the filter unit 100, respectively.

The filter unit 100 comprises a filter material 101 that is porous and therefore (partially) permeable to a fluid like a sample of blood. As can be seen from FIG. 2, the filter material 101 is provided as an approximately circular disk. This disc of filter material 101 fits into an associated aperture A' of an "intermediate foil" 104.

Moreover, the filter unit 100 comprises a top foil 102 and a bottom foil 103, wherein the terms "top" and "bottom" refer to the position of these foils in the drawings. The top and bottom foils 102, 103 have holes or apertures A that are smaller than the disc of the filter material 101, and they are laminated to opposite sides of the aforementioned intermediate foil 104. Accordingly, the top foil 102 and the bottom foil 103 enclose the intermediate foil 104 and the filter material 101. As can be seen from FIG. 1, the filter material 101 is thicker than the intermediate foil 104. It is therefore compressed and bulges (in positive and negative z-direction) within the apertures A of the top and bottom foil.

An experimental blood separation test was performed with a filter unit like that of FIGS. 1-3, comprising a test filter material (Pall Vivid Plasma Separation membrane grade GX; diameter 10 mm) laminated between foils. The sample volume (about 40 μL) used was deliberately chosen too large to provoke edge leakage. However, no leakage was observed (i.e. the outer border of the filter material, which is enclosed between the top and bottom foil, remains substantially dry). Clear plasma was observed at the outlet side of the filter material.

While the filter unit 100 of FIGS. 1-3 consists of three foils, it is clear that lamination of the filter material between just two foils or layers is possible as well. In this case one or both foils will preferably have an embossed structure around the aperture for the filter material.

FIG. 4 shows a cartridge 190 consisting of the filter unit 100 of FIGS. 1-3 and a carrier 150, wherein these two components are shown immediately before they are attached to each other using lamination technology.

The carrier 150 consists of a body 151, which is for example made from transparent plastic by injection molding and which comprises a filter support 153, one or more processing/detection chambers 155, and a channel 154 connecting the support to said chamber(s). Moreover, the carrier 150 comprises a laminate 152 which covers and closes the processing chamber 155 and the associated channel 154.

Figure 5:
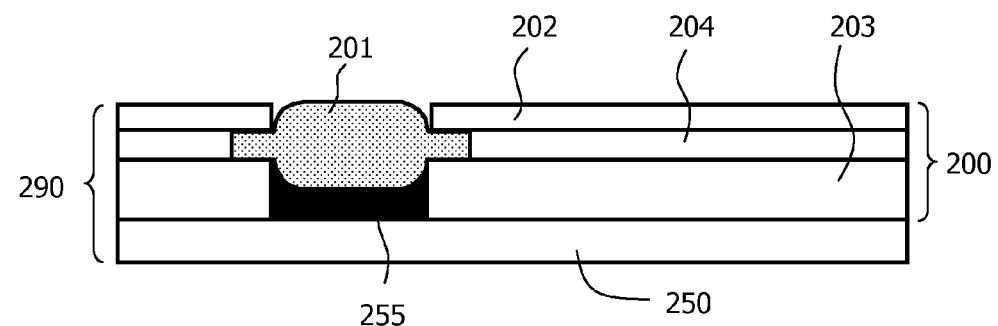
FIG. 5 shows a cross section through a cartridge with a second filter unit comprising foils of different thicknesses.

The embodiment of the filter unit 100 is symmetric in the sense that the geometry of the apertures A and the thicknesses of the top and bottom foils 102, 103 are identical. In practice, it can be advantageous to choose an asymmetric structure (different aperture diameter, different foil thicknesses etc.). FIG. 5 shows an exemplary cartridge 290 with a filter unit 200 having an asymmetric design: the bottom foil 203 is thicker than the top foil 202 (and the intermediate foil 204). Asymmetry can be deliberately introduced by the order in which the lamination is executed or by the asymmetric nature of the filter material itself. Asymmetric situations will generally result in doming of the filter material, upwards or downwards. This doming can be used to enhance the good contact that is normally required between the filter material and the filter support. Especially in the situation of a blood separation filter combined with a very limited sample volume it is advantageous to strictly reduce the dead volume between filter and filter support to a minimum.

The carrier 250 that is attached to the filter unit 200 creates a processing chamber 255 immediately adjacent to the exit side of the filter material 201. Hence no fluid is lost for a transport from the filter to the processing chamber. The carrier 250 may for example be a rigid component (e.g. an injection molded plastic part), or an additional foil.

Figure 6:
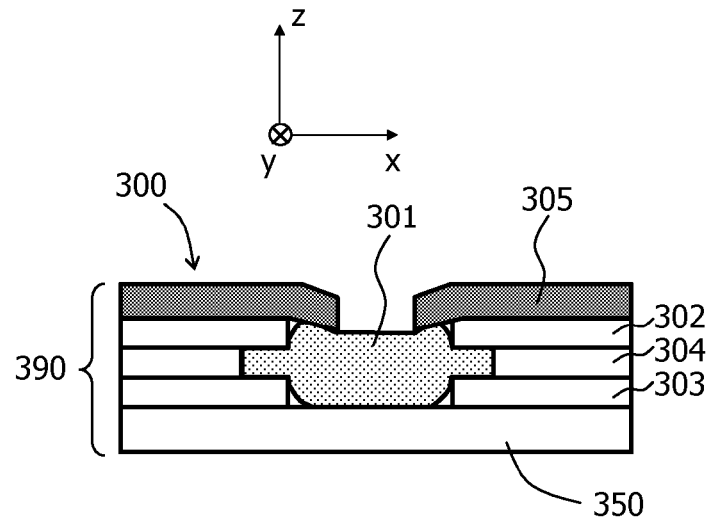
FIG. 6 shows a cross section through a cartridge comprising a third filter unit with an additional top foil for holding the filter material.
Figure 7:
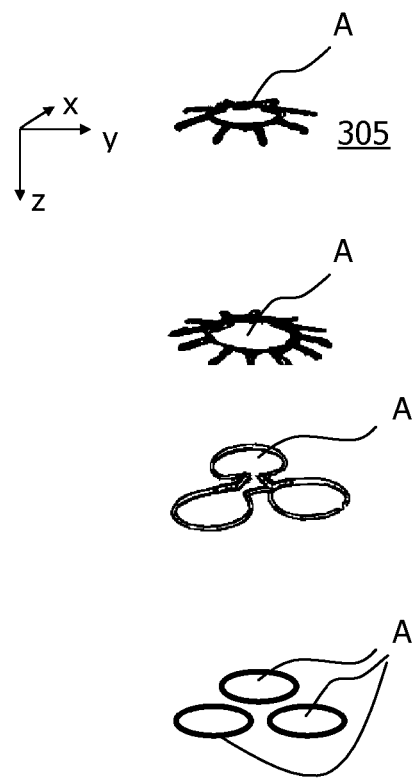
FIG. 7 shows views onto the bottom side of four embodiments of the additional top foil of the cartridge of FIG. 6, said embodiments comprising apertures with radial slots, an aperture composed of three connected small circular openings, and an aperture composed of three unconnected small circular openings, respectively.

FIGS. 6 and 7 illustrate another method to guarantee a good physical contact between the filter material 301 of a filter unit 300 and the filter support on a carrier 350. Here, an additional top layer or top foil 305 is added as a "holding element" with the function to press the filter material 301 down towards the filter support.

Four exemplary options for the design of the aperture A in the additional top foil 305 that can be used to guarantee good physical contact between the filter and the filter support are shown in FIG. 7. In the upper two drawings, the aperture A in the additional top foil 305 is surrounded by radial slots or cuts that allow to bend the ring-shaped border of the aperture downwards (it should be noted that the drawings show the additional top foil upside down).

In the third drawing from the top of FIG. 7, a single aperture A is composed of three separate small circular openings or holes that are connected by a central hole. This results in three fingers that can be deformed to press the filter material on the filter support in the centre of the filter.

In the lowermost drawing of FIG. 7, the whole aperture A consists of three separate (unconnected) circular holes. Hence the additional top foil is flat by itself but prevents domed filters to take a domed shape in the wrong direction when pressed against the filter support. Moreover, such an additional top foil also helps to prevent touching of the filter material. A foil thickness of about 0.3 mm combined with holes of 3 mm diameter protects the filter quite adequately against touching with a finger.

Figure 8:
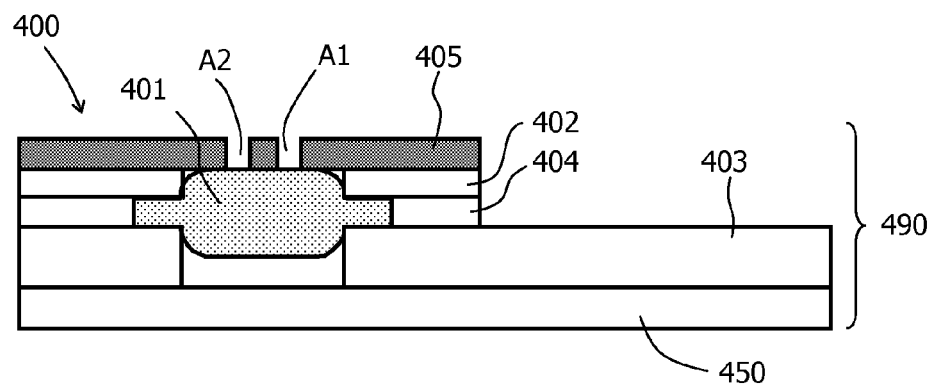
FIG. 8 shows a cross section through a cartridge comprising a fourth filter unit with a bottom foil that is larger to cover an associated carrier and with an additional top foil having several openings.

FIG. 8 shows a fourth embodiment of a filter unit 400 in which the bottom foil 403 has a larger area than the top foil 402 and the intermediate foil 404 above it. Such a large bottom foil 403 can be used to close open cavities (not shown) when it is attached to a carrier 450. Moreover, the filter unit 400 comprises an additional top foil 405 having several apertures A1, A2 above the filter material 401 to prevent touching of the filter material and to bend it downwards.

Figure 9:
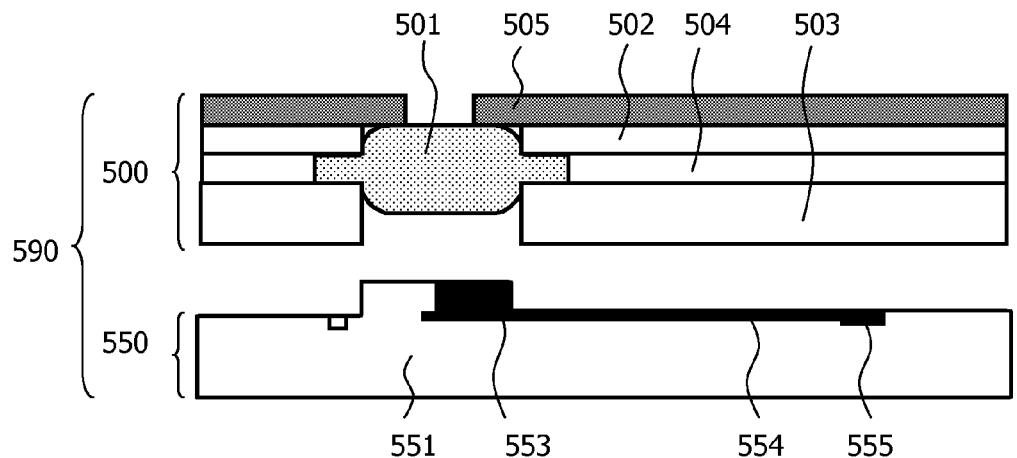
FIG. 9 shows a cross section through a cartridge comprising a fifth filter unit before the attachment of the filter unit to the carrier, wherein the bottom foil of the filter unit covers open cavities of the carrier.

The filter unit 500 shown in FIG. 9 is similar to that of the FIG. 8 but with all four foils 502, 503, 504, and 505 extending over the whole area of the associated carrier 550. It can be seen that the bottom foil 503 adopts the function of the standard laminate that closes the channels and the detection chambers of the injection molded carrier 550. Hence two functions are combined here in a single foil-based subunit. The carrier 550 still contains the plasma drain channel 554 and detection chambers 555 on the right hand side. Filter unit 500 and injection molded carrier 550 are attached to each other to constitute the final cartridge 590.

Figure 10:
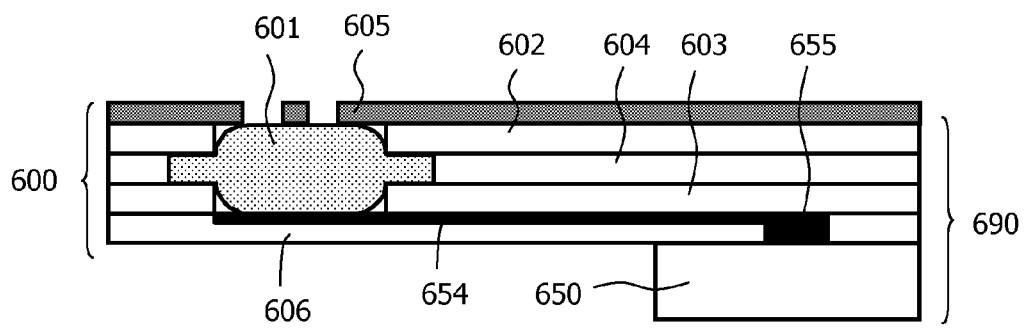
FIG. 10 shows a cross section through a cartridge comprising a sixth filter unit with a post-treatment fluidic system.

FIG. 10 shows another embodiment of a cartridge 690 comprising a filter unit 600 and a carrier 650. Here, the filter unit 600 consists of the following components (from top to bottom):
  an additional top layer 605 for holding the filter material down;
  a top foil 602 with an aperture;
  an intermediate foil 604 with an aperture that contains the filter material 601, for example a blood separation filter;
  a bottom foil 603 with an aperture;
  an additional bottom foil 606.

The additional bottom foil 606 comprises a plasma drain channel 654 and a processing chamber 655 (realized as an aperture or hole in the foil). The drain channel 654 bridges the distance between the filter position and the processing chamber 655. A filter support structure and the plasma drain channel 654 may be embossed in the additional bottom foil 606 (and/or the bottom foil 603).

The injection molded carrier 650 serves as an optical detection part that is reduced in size to the detection zone. The reduced size allows a faster and more cost effective manufacturing. The use of high grade optical material for the injection molding of the carrier 650 is reduced in this way.

Figure 11:
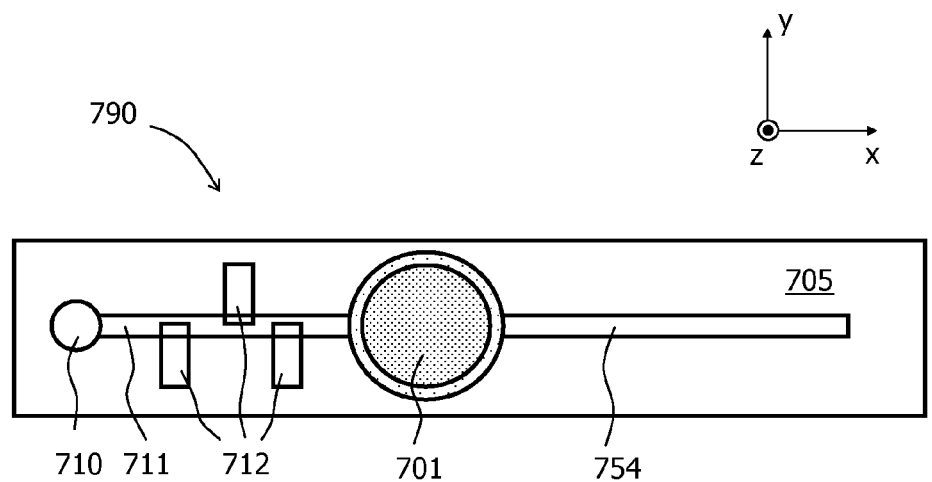
FIG. 11 shows a top view onto a cartridge comprising a seventh filter unit and an associated carrier, wherein the filter unit has a pre-treatment and a post-treatment fluidic system.
Figure 12:
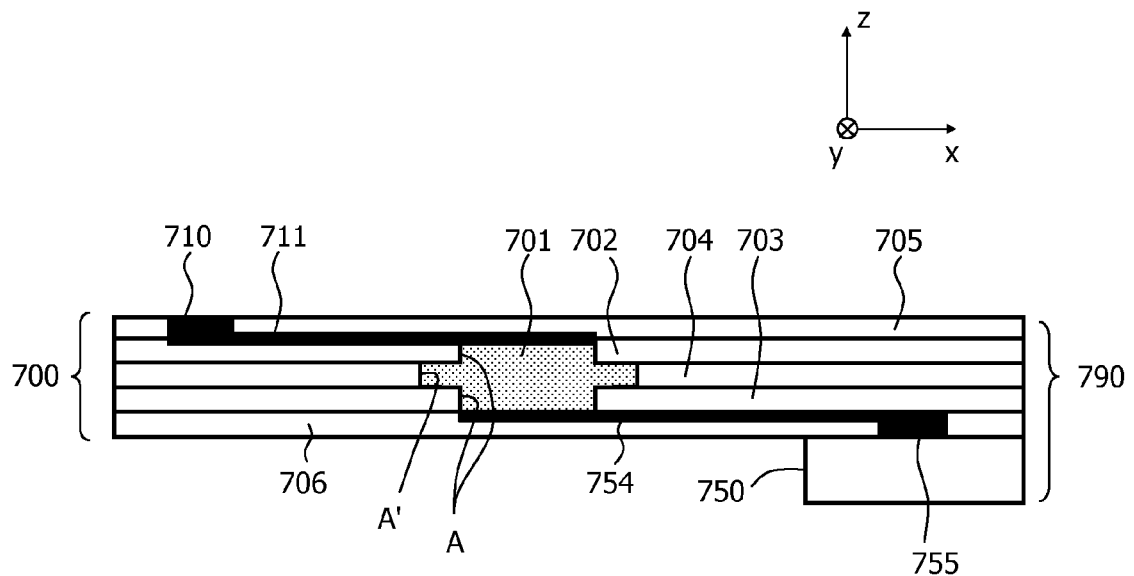
FIG. 12 shows a cross section through the cartridge of FIG. 11.

FIGS. 11 and 12 show a top view onto and a cross section through a cartridge 790 comprising a seventh embodiment of a filter unit 700 and an associated carrier 750, wherein the filter unit has a pre-treatment and a post-treatment fluidic system. The filter unit 700 comprises the (blood) filter material 701 that is arranged in an intermediate foil 704 and laminated between a top foil 702 and a bottom foil 703.

Moreover, an additional top foil 705 is provided on the top foil 702. This additional top foil 705 comprises a "pre-treatment fluidic system" with a blood deposition hole 710 and an integrated blood supply channel 711 that connects this hole 710 to the blood separation filter 701. The blood supply channel 711 also serves to fill specific detection chambers 712 for blood (schematically represented by the rectangular structures in FIG. 11).

Furthermore, an additional bottom layer 706 is provided that comprises a "post-treatment fluidic system" with a plasma drain channel 754 and a plasma detection chamber 755. The channel 754 supplies plasma to the detection chamber 755 on the right hand side. This part is similar to that of FIG. 10.

The main objective of this embodiment is to use a single (fingerprick) blood sample with a limited total sample volume for both measurements in blood and plasma. Another advantage of such a structure is that the filter material 701 is brought closer to the plasma detection area 755, thus reducing the volume of plasma needed. This is because the distance between the sample deposition area 710 and the detection area 755 does not have to be bridged by a long plasma channel filled with plasma that is not used in a test.

An example of an application of the cartridge 790 is that one or several of the blood detection chambers 712 (or the channel 711 itself) is used for electrochemistry, while the plasma in the post-treatment fluidic system is used for detection of proteins. In order to realize electrochemical detection procedures, screen-printed electrodes as they are used in microscale electrochemistry can for example be realized on one of the foils (e.g. 705, 702) used in the lamination process.

The components used in the pretreatment of a blood separation filter can be incompatible with electrochemical measurements in blood. A way to cope with this kind of interferences is to fluidically separate the filter material 701 and the detection chambers 712, 755 for blood and plasma.

It should be noted that the provision of a pre-treatment fluidic system and a post-treatment fluidic system which are coupled by a fluid-treatment element is an independent aspect of the invention.

In this example the size of the injection molded carrier 750 for optical detection can also be reduced to a minimum as the majority of the functionality is transferred to the laminated structure of the filter unit 700.

Figure 13:
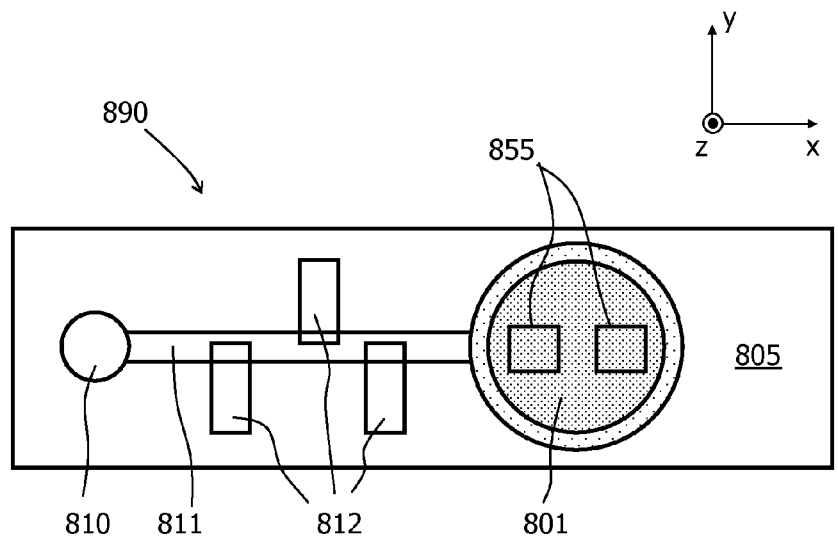
FIG. 13 shows a top view onto a cartridge comprising an eighth filter unit with a pre-treatment fluidic system, wherein processing chambers are located adjacent to the filter material.
Figure 14:
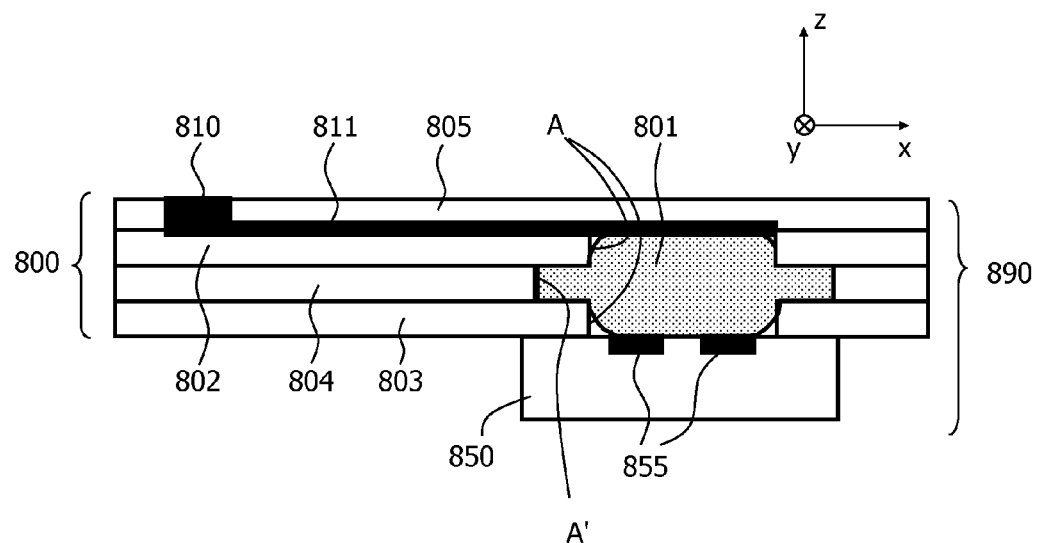
FIG. 14 shows a cross section through the cartridge of FIG. 13.

FIGS. 13 and 14 show a cartridge 890 that is a modification of the cartridge of FIGS. 11 and 12. Again there is a combination of a laminated filter material 801 and a pre-treatment fluidic system, the latter comprising an integrated blood supply channel 811 between a blood deposition hole 810 and the filter material.

The components that are different relate to the post-treatment fluidic system behind the filter material 801. In particular, processing chambers 855 are formed in the carrier 850 which is attached at the aperture in the bottom foil 803. Hence the processing chambers 855 with the detection area for plasma are directly under the blood separation filter material 801.

One objective of the cartridge 890 is to allow detection of target molecules and/or electrochemical properties in both blood and plasma. Moreover, the proposed structure brings the filter material 801 closer to the plasma detection area 855 to reduce the volume of plasma needed. The distance between the sample deposition area 810 and the detection area 855 does not have to be bridged by a plasma channel filled with plasma that is not used in a test. Instead, optimal use of the plasma generated is made and the required sample volume is reduced to a minimum. Another important advantage is that the time between sample deposition and the arrival of plasma in the detection zone is reduced. As soon as the filter is wetted with blood, the first plasma arrives almost instantaneously at the bottom side of the filter. Moreover, a considerable fraction of the cartridge 890 can be made in a roll-to-roll technology which is meant to reduce the overall costs.

It should be noted that the arrangement of a processing chamber (e.g. 855) immediately adjacent to a fluid-treatment element (e.g. the filter material 801) is an independent aspect of the invention.

In principle it is also possible to distribute the fluid to be filtered (e.g. blood) over several separation filters. This can for instance be useful if the chemical pre-treatment components present in a blood separation filter for one test are incompatible with the components used in the filter or detection area for another test.

Figure 15:
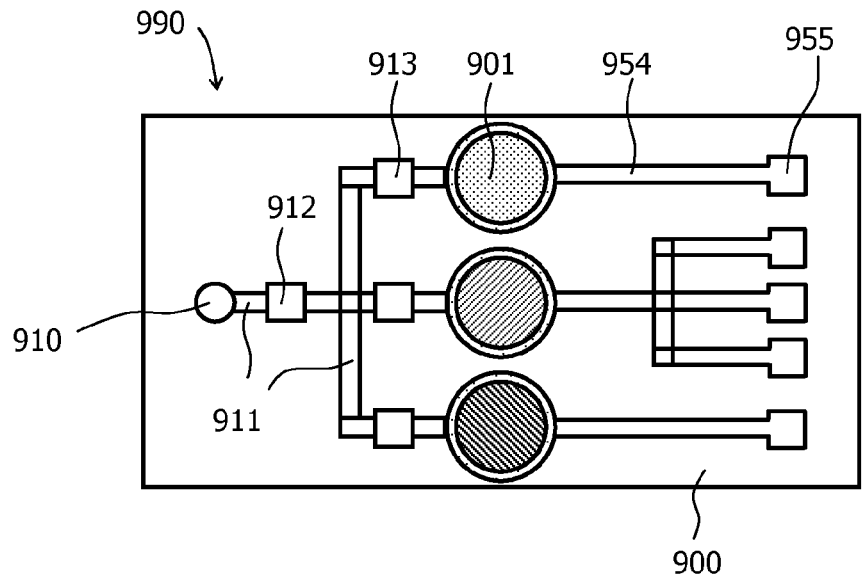
FIG. 15 shows a top view onto a cartridge similar to that of FIGS. 11 and 12 but with a pre-treatment fluidic system that splits into three parallel branches.

FIG. 15 shows a top view onto a cartridge 990 that is an application of the aforementioned principle to the cartridge of FIGS. 11 and 12. The cartridge 990 comprises a pre-treatment fluidic system with an inlet 910 (blood deposition position) and an associated channel 911 that splits into three branches. One or more detection chambers 912 (for blood) can be coupled to the channel 911 before the branching point, and one or more detection chambers 913 (for blood) can be coupled to the branches of the channel 911 after the branching point.

Each branch of the channel 911 leads to another filter (sub-) unit with (different) filter materials 901. Moreover, a separate post-treatment fluidic system with channels 954 and detection chambers 955 (for plasma) is provided behind each filter material 901. As exemplarily shown for one of these channels 954, branching can occur in these channels, too.

Figure 16:
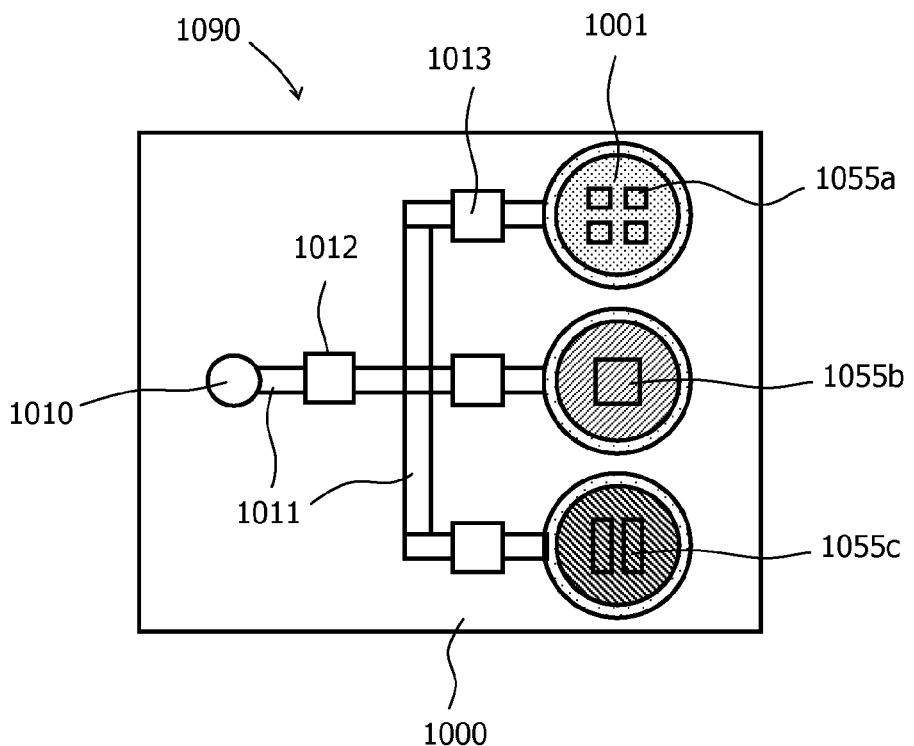
FIG. 16 shows a top view onto a cartridge similar to that of FIGS. 13 and 14 but with a pre-treatment fluidic system that splits into three parallel branches.

FIG. 16 shows a top view onto a cartridge 1090 that is an application of the above mentioned principle to the cartridge of FIGS. 13 and 14. The cartridge 1090 comprises a pre-treatment fluidic system with an inlet 1010 (blood deposition position) and an associated channel 1011 that splits into three branches. One or more detection chambers 1012 (for blood) can be coupled to the channel 1011 before the branching point, and one or more detection chambers 1013 (for blood) can be coupled to the branches of the channel 1011 after the branching point. The cartridge 1090 allows the distribution of blood over several different blood separation filters. This can be useful if e.g. the chemical pre-treatment components present in the blood separation filter for one test are incompatible with the components used in the filter or detection area for another test. Detection areas 1055a, 1055b, 1055c for plasma directly under the filter materials 1001 are represented by rectangles in FIG. 16. The detection may for example comprise the detection of target molecules and/or of electrochemical properties.

A key feature of the cartridges 790, 890, 990, and 1090 of FIGS. 11-16 is the simultaneous detection in blood and plasma originating from the same blood sample. The cartridge designs are simple and inexpensive as several functions (capillary fluid transport, filter mounting, separation of blood and plasma, simultaneous detection in blood and plasma) are combined using lamination technology. This allows cost-effective mass production of disposable cartridges on a roll-to-roll basis.

An additional key feature of the cartridges 990 and 1190 of FIGS. 13, 14, and 16 is a biosensor cartridge with a detection area for plasma directly under the blood separation filter.

For a reliable progress of the test procedure it is often important to deposit a specified sample volume between a minimum value and a maximum value. In practice, there is however often an uncertainty whether or not the right amount of sample has been deposited on a biosensor cartridge in case of sample deposition without the use of a sample volume measuring device. One important example is the direct blood deposition from a finger (after a fingerprick) on a cartridge. In this case only visual control is possible.

As a solution to the aforementioned problem, an additional top layer may be added on top of the filter material (or, more generally, on top of a sample deposition pad or structure) with one or several sample deposition holes. By a proper choice of e.g. the thickness of the additional top layer and the diameter of the sample deposition hole(s), the difference in visual appearance between a minimal and maximum deposited sample volume can be pronounced. This allows visual control of deposited sample volume even for the difficult situation of direct blood deposition from a finger after a fingerprick.

Figure 17:
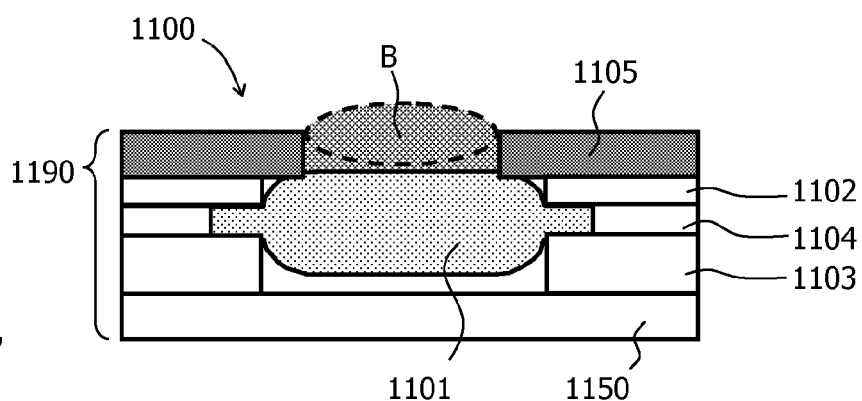
FIG. 17 shows a cross section through a cartridge comprising an eleventh filter unit that allows for the application of a sample liquid under visual control, showing the case in which a maximal amount of fluid is applied.
Figure 18:
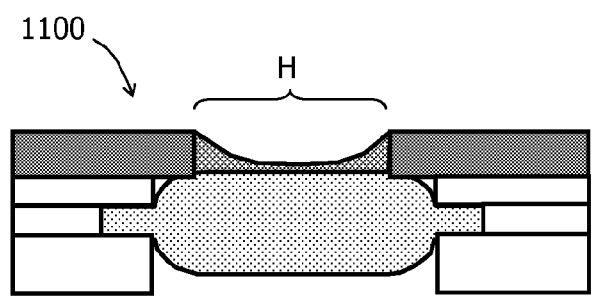
FIG. 18 shows the cartridge of FIG. 17 when a minimal amount of fluid is applied.

FIGS. 17 and 18 illustrate the aforementioned approach, showing a cross section through a filter unit 1100 that comprises a filter material 1101 mounted using lamination technology such that it is encompassed by a top foil 1102 and a bottom foil 1103. An additional top layer 1105 is provided to pronounce the difference between the situations when a maximum volume of a sample B (e.g. 30 μL; FIG. 17) and when a minimal sample volume (e.g. 20 μL; FIG. 18) has been added. The thickness of the additional top layer 1105 and the diameter of its deposition hole H are chosen such that the difference in maximum and minimum sample volume can easily be judged visually after blood separation. This allows visual control of deposited sample volume even for the difficult situation of direct blood deposition from a finger.

In particular, the recess H in the additional top layer 1105 should be large enough to accommodate the total sample volume range. By making the hole diameter smaller than the diameter of the filter material 1101, the visual difference between the extremes can be enlarged. The dashed line in FIG. 17 indicates the difference in volume between minimum and maximum volume of sample B. The maximum volume is achieved if no further sample fluid can be held by molecular adhesion forces.

Whether or not enough blood has been deposited can hence be judged from the presence of at least a concave meniscus in the sample deposition hole. In case of maximum blood deposition, a strongly convex meniscus is formed. The total filter area should be wetted with blood, although the layer in the centre may be thin. If less than the minimal sample volume is added, the (e.g. white) filter material clearly becomes visible through the sample blood layer in the centre of the filter.

The additional top layer 1105 can best be hydrophobic to pronounce this effect. The visual evaluation can be based on the color of the central area of the filter and/or on the shape of the blood meniscus. The shape of the meniscus is seen best by observing it under an oblique angle. The convex blood meniscus that occurs in case of sufficient sample deposition even contributes to the capillary forces that drive the blood separation.

If needed, the total sample volume range that can be visually judged can be reduced by use of more than one deposition hole above the same filter material.

While the aforementioned embodiment has been described for a situation of fingerprick blood deposition on a blood separation filter, it is clear that similar issues play a role for other systems without blood separation filter (e.g. direct detection of biomarkers in blood). There the blood separation filter will be replaced by another type of sample deposition pad or structure.

An additional advantage of the cover layer on top of the filter is protection of the filter against unintentional touching. Moreover, the cover layer can also be used to improve and guarantee the physical contact between the filter and the filter support under the filter.

Features of the embodiments described above can be combined and/or modified in various ways.

For example, the filling of the cartridges was assumed to be based on autonomous, capillary driven fluid flow. It is however also possible to stimulate fluid flow by applying over-pressure on the inlet side, under-pressure on the vent side of the cartridge, or by mechanical stimulation of fluid flow by cartridge manipulation (i.e. peristaltic flow generated by the user or the analyzer).

Another possible modification comprises the deposition of samples. In the above examples, capillary pick-up by an inlet port at a front side of the cartridge and by associated channels in a (top) foil has been described. Alternatively, capillary pick-up of a sample could take place at the side (like in a glucose strip). The filter material could for example be accessible at a side face of a filter unit, e.g. between the top and bottom foil, allowing to apply sample to it through this side.

Moreover, the examples given above were mostly explained with respect to blood samples (of biological or non-biological origin) and blood separation filters. It is however clear that the scope of the invention includes other samples and filters, too. Accordingly, the described devices and procedures can generally be used to treat (e.g. filter) a "raw fluid", wherein the "treated fluid" may then further be processed in the same device.

The advantages of the use of a (partly) foil based cartridge will steadily increase with the increasing number of technologies that become available on foil (e.g. conductive patterns, RF-IDs, screen printed electrodes for electrochemistry, advanced hot embossing patterns, etc.).

It should be noted that the part in front of the filter material of any shown embodiment can be combined with the part behind the filter material of any other shown embodiment of the invention. Similarly, any described filter unit 100, 200, . . . 1100 can be combined with any described carrier 150, 250, . . . 1150.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A cartridge for processing a fluid, comprising:
  a) a pre-treatment fluidic system that comprises an inlet via which the fluid can be supplied and at least one primary detection chamber in which said fluid can be measured;
  b) a post-treatment fluidic system that comprises at least one secondary detection chamber in which fluid can be measured; and
  c) a fluid-treatment element that is permeable to at least a part of the fluid and that couples the post-treatment fluidic system to the pre-treatment fluidic system, wherein the at least a part of the said fluid that passes through the fluid-treatment element comprises post-treated fluid, and wherein a measurement of said fluid in the at least one primary detection chamber and a measurement of the post-treated fluid in the at least one secondary detection chamber can occur simultaneously for at least a part of a respective measurement duration.

2. A method for the processing of a fluid in a cartridge according to claim 1, said method comprising the following steps:
  a) introducing into the inlet of the cartridge a quantity of the fluid that fills both the pre-treatment fluidic system and the post-treatment fluidic system;
  b) measuring the fluid in the primary detection chamber of the cartridge; and
  c) measuring the fluid in the secondary detection chamber of the cartridge.

3. The cartridge according to claim 1, wherein a total volume of the pre-treatment fluidic system and the post-treatment fluidic system is a smaller than 500 µl.

4. The method according to claim 2, wherein measuring the fluid in the primary detection chamber comprises measuring the fluid to obtain at least one selected from the group consisting of electrochemical measurements, electrical impedance measurements, heat conduction measurements, optical measurements, and spectroscopic measurements.

5. A cartridge for processing a fluid, comprising:
  a) a pre-treatment fluid system that comprises an inlet via which the fluid can be supplied and at least one primary detection chamber in which said fluid can be measured;
  b) a post-treatment fluidic system that comprises at least one secondary detection chamber in which fluid can be measured; and
  c) a fluid-treatment element that is permeable to at least a part of the fluid and that couples the post-treatment fluidic system to the pre-treatment fluidic system, wherein the secondary detection chamber comprises a transparent side face that allows optical examination of the fluid in the secondary detection chamber, wherein the optical examination includes examination of fluid directly adjacent to the transparent side face by at least one or more selected from the group of consisting of evanescent field excitation, observation of scattered light, and frustrated total internal reflection.

6. The cartridge according to claim 1, wherein the fluid-treatment element is a filter element.

7. The method according to claim 2, wherein the fluid comprises blood.

8. The cartridge according to claim 1, wherein the pre-treatment fluid system, the post-treatment fluidic system, and the fluid-treatment element are embodied within a structure that comprises a rigid carrier attached to a filter unit for filtering the fluid, wherein said filter unit comprises:
  a) at least one foil that is impermeable to the fluid, the at least one foil having at least one aperture; and
  b) a filter material that is permeable to at least a part of the fluid, wherein said filter material is integrated into said at least one aperture of the at least one foil, wherein the filter material serves as the fluid-treatment element.

9. The cartridge according to claim 8, wherein the filter material is arranged in an aperture of an intermediate foil that is embedded between a top foil and a bottom foil.

10. The cartridge according to claim 8, wherein the at least one foil of the filter unit comprises at least one cavity, wherein the at least one cavity is selected from the group consisting of (i) a supply channel, (ii) the at least one primary detection chamber, (iii) a drain channel, and (iv) the at least one secondary detection chamber.

11. The cartridge according to claim 8, wherein the filter material has a dome shape.

12. A cartridge for processing a fluid, comprising:
a) a pre-treatment fluidic system that comprise an inlet via which the fluid can be supplied and at least one primary detection chamber in which said fluid can be measured;
b) a post-treatment fluidic system that comprise at least one secondary detection chamber in which fluid can be measured; and
c) a flud-treatment element that is permeable to at least a part of the fluid and that couples the post-treatment fluidic system to the pre-treatment fluid system,
wherein the pre-treatment fluid system, the post-treatment fluidic system, and the fluid-treatment element are embodied within a structure that comprises a rigid carrier attached to a filter unit for filtering the fluid, wherein said filter unit comprises;
(i) at least one foil that is impermeable to the fluid, the at least one foil having at least one aperture; and
(ii) a filter material that is permeable to at least a part of the fluid, wherein said filter material is integrated into said at least one aperture of the at least one foil, wherein the filter material serves as the fluid-treatment element, further comprising:
a holding element for pressing the filter material in one direction, wherein said holding element comprises an additional foil.

13. The cartridge according to claim 8, wherein the carrier comprises at least one cavity for an accommodation of fluid, wherein said cavity is connected to the filter material.

14. The cartridge according to claim 13, wherein the at least one cavity of the carrier is covered by a foil of the filter unit.

15. The cartridge according to claim 1, wherein the at least one secondary detection chamber is located adjacent to the fluid-treatment element.

16. The cartridge according to claim 1, wherein a total volume of the pre-treatment fluidic system and the post-treatment fluidic system is a smaller than 50 µl.

17. The cartridge according to claim 1, wherein the secondary detection chamber comprises a transparent side face that allows optical examination of the fluid in the secondary detection chamber, wherein the optical examination includes examination of fluid directly adjacent to the transparent side face by at least one or more selected from the group consisting of evanescent field excitation, observation of scattered light, and frustrated total internal reflection.

18. The cartridge according to claim 8, further comprising a holding element for pressing the filter material in one direction, wherein said holding element comprises an additional foil.

* * * * *